United States Patent [19]

Lozier et al.

[11] Patent Number: 5,437,671
[45] Date of Patent: Aug. 1, 1995

[54] PERPENDICULAR ROD CONNECTOR FOR SPINAL FIXATION DEVICE

[75] Inventors: Antony J. Lozier, Warsaw, Ind.; John R. Johnson; John R. Dimar, II, both of Louisville, Ky.

[73] Assignee: Zimmer, Inc., Warsaw, Ind. ; a part interest

[21] Appl. No.: 192,871

[22] Filed: Mar. 7, 1994

Related U.S. Application Data

[62] Division of Ser. No. 848,904, Mar. 10, 1992, abandoned.

[51] Int. Cl.⁶ ............................................. A61B 17/56
[52] U.S. Cl. ..................................................... 606/61
[58] Field of Search ................ 606/62, 61, 69, 70, 606/71, 72, 73; 623/16, 17

[56] References Cited

U.S. PATENT DOCUMENTS

| 2,372,866 | 4/1945 | Tofflemire | 128/76 |
|---|---|---|---|
| 2,774,350 | 12/1956 | Cleveland | 128/92 |
| 4,269,178 | 5/1981 | Keene | 128/69 |
| 4,289,123 | 9/1981 | Dunn | 128/84 |
| 4,361,141 | 11/1982 | Tanner | 128/69 |
| 4,411,259 | 10/1983 | Drummond | 128/69 |
| 4,433,676 | 2/1984 | Bobechko | 128/69 |
| 4,433,677 | 2/1984 | Ulrich | 128/69 |
| 4,570,618 | 2/1986 | Wu | 128/69 |
| 4,658,809 | 4/1987 | Ulrich | 128/69 |
| 4,738,251 | 4/1988 | Plaza | 128/69 |
| 4,743,260 | 5/1988 | Burton | 623/17 |
| 4,805,602 | 2/1989 | Puno | 128/69 |
| 4,815,453 | 3/1989 | Cotrel | 128/69 |
| 4,827,918 | 5/1989 | Olerud | 128/92 |
| 4,875,471 | 10/1989 | Plaza | 128/69 |
| 4,887,596 | 12/1989 | Sherman | 606/61 |
| 4,944,743 | 7/1990 | Gotzen et al. | 606/61 |
| 4,946,458 | 8/1990 | Harms | 606/61 |
| 4,950,269 | 8/1990 | Gaines, Jr. | 606/61 |
| 5,000,166 | 3/1991 | Karpf | 128/69 |
| 5,007,909 | 4/1991 | Rogozinski | 606/61 |
| 5,010,879 | 4/1991 | Moriya | 128/69 |
| 5,011,484 | 4/1991 | Breard | 606/61 |
| 5,030,220 | 7/1991 | Howland | 606/61 |
| 5,067,955 | 11/1991 | Cotrel | 606/61 |
| 5,102,412 | 4/1992 | Rogozinski | 606/61 |

FOREIGN PATENT DOCUMENTS

| 89111342 | 6/1989 | European Pat. Off. | A61K 47/48 |
|---|---|---|---|
| 2642642 | 8/1990 | France | A61B 17/58 |
| 0961182 | 5/1983 | U.S.S.R. | A61B 17/18 |
| PCT/EP89/-00802 | 7/1989 | WIPO | A61F 5/02 |
| PCT/FR90/-00539 | 7/1990 | WIPO | A61B 17/60 |

Primary Examiner—Michael A. Brown
Attorney, Agent, or Firm—Todd A. Dawson

[57] ABSTRACT

The spinal rod system and perpendicular rod connector of the invention provides for a first rod to be connected by two pedicle screws transverse to the spine across a vertebra. The perpendicular connector is then connected to the first rod anywhere along the rod. The longitudinal spinal rod is then connected to the perpendicular rod connector using common connectors. The perpendicular connector is slidable along the first rod. By using the perpendicular rod connector, the amount of bending and the tolerances required is reduced as the connector may be slid along the transverse rod to accommodate the longitudinal rod. Known pedicle screws may be used with a slight bend placed in the transverse rod to accommodate the spinal column. Alternatively, the pedicle screws may be bent slightly such that a straight transverse rod may be used. By using the perpendicular rod connector and transverse rod arrangement, the amount of bending required on the longitudinal rod may be reduced to thereby shorten the entire procedure.

3 Claims, 2 Drawing Sheets

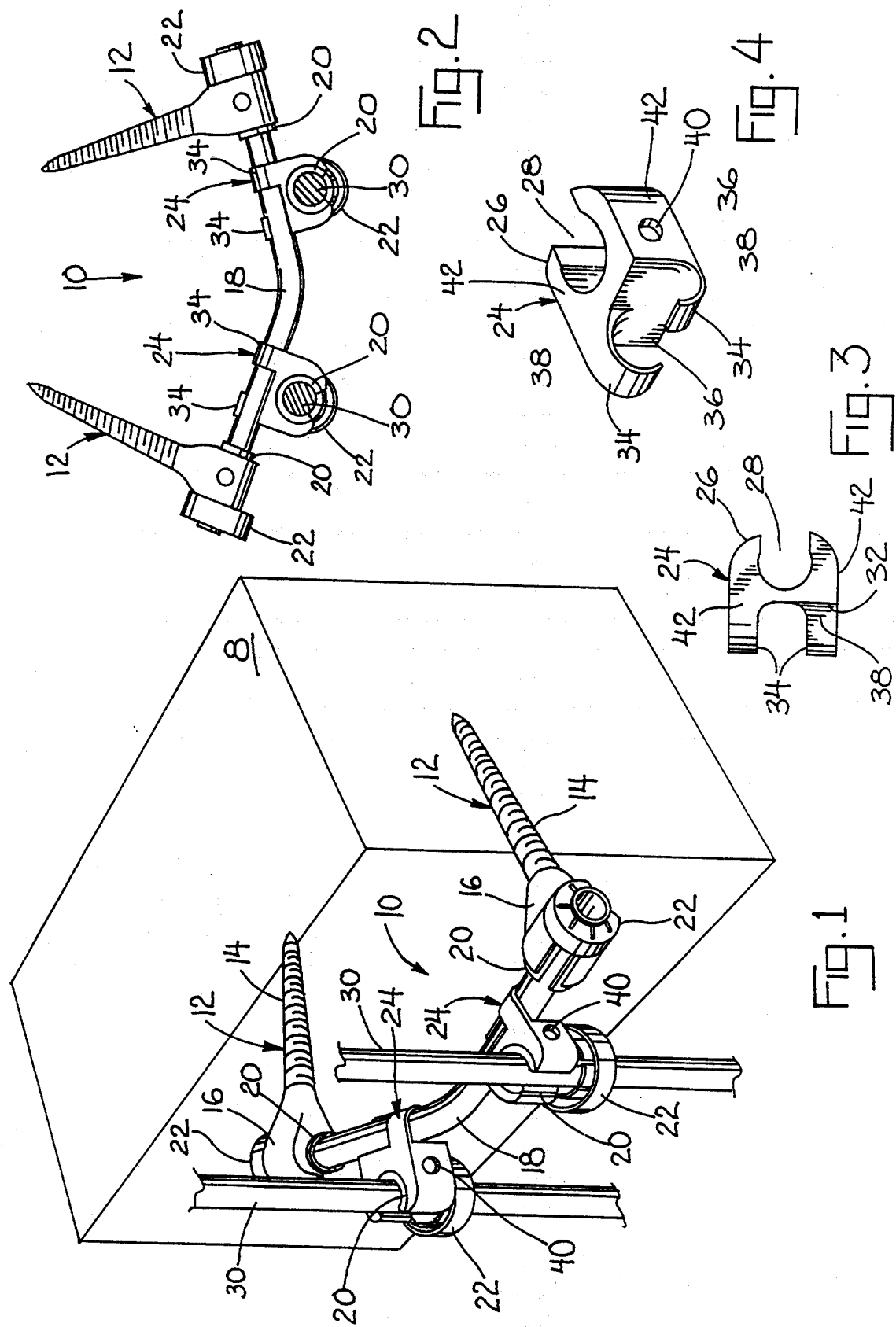

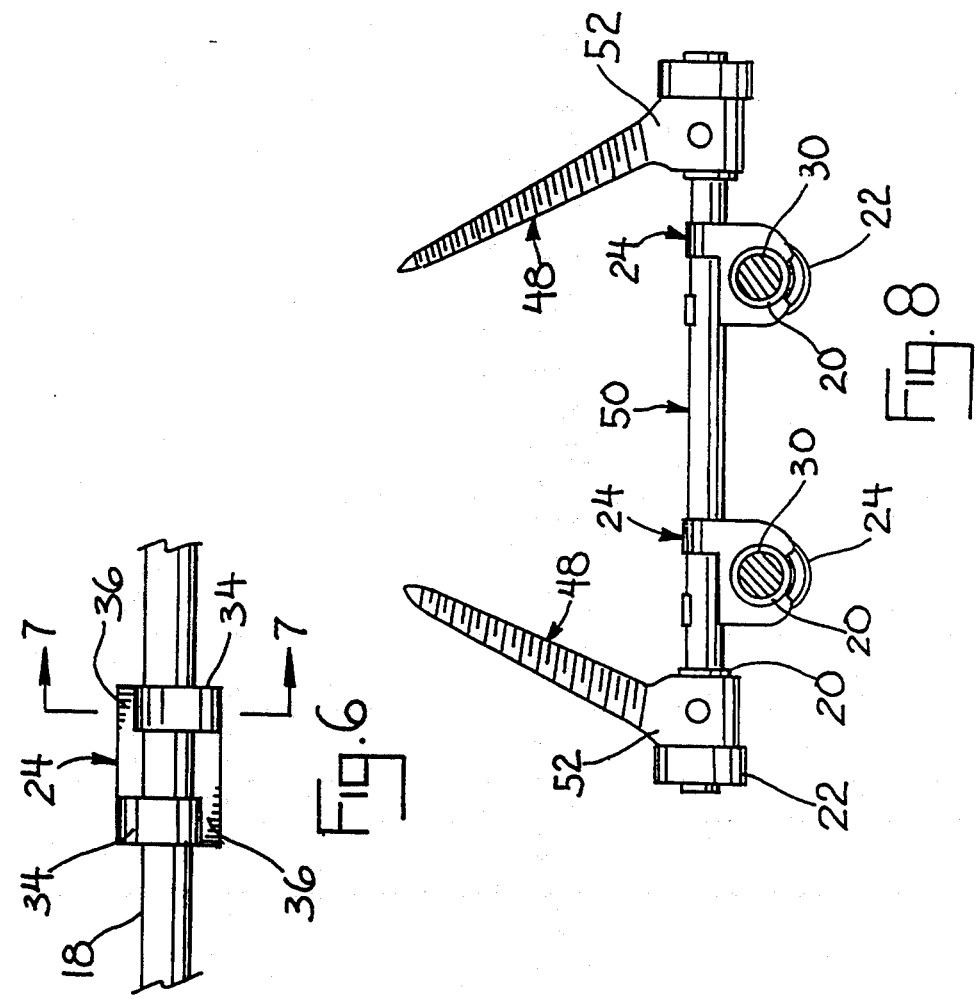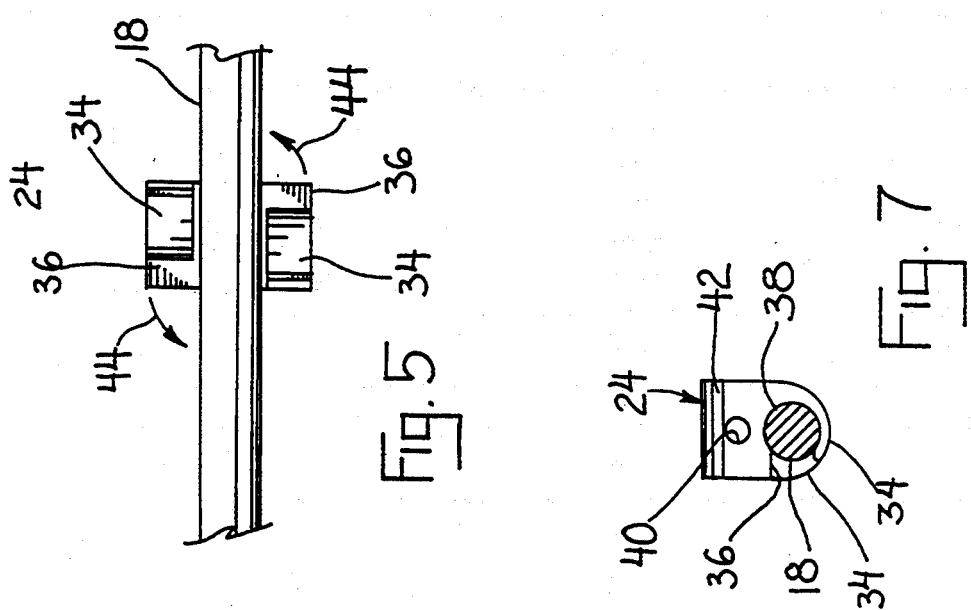

5,437,671

PERPENDICULAR ROD CONNECTOR FOR SPINAL FIXATION DEVICE

This is a division of application Ser. No. 07/848,904 filed Mar. 10, 1992, now abandoned.

FIELD OF THE INVENTION

This invention relates to spinal fixation devices and has specific reference to a spinal rod system which connects a spinal rod to a primary fixation rod and positions the two rods at a ninety degree relationship to one another.

BACKGROUND OF THE INVENTION

It is well known in the correction of spinal deformities to affix a rod or pair of rods longitudinally to the spinal column with a plurality of spinal hooks or pedicle screws. Tension or compression force is applied to the rod between each consecutive screw or hook to correct the deformity. It is further common to cross link or interconnect the longitudinal rods to provide additional stabilization or to engage the spinous process. During the surgical procedure to connect the spinal rods to the spine, the surgeon must bend the spinal rods to conform, generally, to the curvature of the spine. Quite often this requires the surgeon to bend the rod in three dimensions. Since the rods must be connected to a pedicle screw or spinal hook, the tolerances for the bend is exacting. The bending of the rods within the tight space available and to tolerance adds a significant amount of time to an already lengthy surgery.

SUMMARY THE INVENTION

The spinal rod system and perpendicular rod connector of the invention provides for a first rod to be connected by two pedicle screws transverse to the spine across a vertebra. The perpendicular connector is then connected to the first rod anywhere along the rod. The longitudinal spinal rod is then connected to the perpendicular rod connector using common connectors. The perpendicular connector is slidable along the first rod. By using the perpendicular rod connector, the amount of bending and the tolerances required is reduced as the connector may be slid along the transverse rod to accommodate the longitudinal rod. Known pedicle screws may be used with a slight bend placed in the transverse rod to accommodate the spinal column. Alternatively, the pedicle screws may be bent slightly such that a straight transverse rod may be used. By using the perpendicular rod connector and transverse rod arrangement, the amount of bending required on the longitudinal rod may be reduced to thereby shorten the entire procedure.

Accordingly, it is an object of the invention to provide for a novel system for connecting a spinal rod to a spinal column.

Another object of the invention is to provide for a novel perpendicular rod connector.

Another object of the invention is to provide for a primary fixation rod connected transversely to the spinal column.

Another object of the invention is to provide for a novel pedicle screw having a head angled relative to the screw shaft.

Other objects of the invention will become apparent upon a reading of the following description taken along with the accompanying drawings.

BRIEF DESCRIPTION OF THE DRAWINGS

FIG. 1 is a perspective view of the invention connected to a vertebra represented by a solid block and the spinal rods partially shown.

FIG. 2 is an elevational view of the invention with the spinal rods shown in cross section.

FIG. 3 is an elevational view of the perpendicular rod connector of the invention.

FIG. 4 is a perspective view of the perpendicular rod connector of FIG. 3.

FIGS. 5 and 6 are sequential elevational views illustrating the method of connecting the perpendicular rod connector to a spinal rod (partially shown).

FIG. 7 is a view taken along line 7—7 of FIG. 6.

FIG. 8 is an elevational view of the invention in use with an alternative embodiment of the pedicle screws.

DESCRIPTION OF THE PREFERRED EMBODIMENTS

The preferred embodiments herein disclosed are not intended to be exhaustive or to limit the invention to the precise forms disclosed. Rather, they are chosen and described to enable others skilled in the art to utilize their teachings.

The perpendicular rod system 10 is illustrated connected to a block 8 for illustrative purposes only. Block 8 is in place of an actual vertebra well known in the art. Perpendicular rod system 10 includes a pair of pedicle screws 12 each including a threaded shaft 14 for turning into the pedicle of the vertebra and a head 16. Head 16 of each pedicle screw 12 forms a generally C-shaped seat. A rod 18 extends between each pair of pedicle screws 12 and is connected thereto by a sleeve 22 wedged into head 16 and maintained therein by a collar 24. Sleeve 22 and collar 24 engage in a ratchet manner such that collar 24 will not slide off of sleeve 22. As illustrated in FIGS. 1 and 2, rod 20 includes a central bend to conform to the outer geometry of the vertebra just above the spinous process.

Perpendicular rod connector 24 includes a generally C-shaped body 26 defining a central opening 28. Opening 28 accommodates a spinal rod 30 with a sleeve 22 and collar 24 for securement of the rod to the connector 24. Body 26 includes a end wall 32. A pair of arcuate projections 34 extend from opposite side edges of said end wall 32 as illustrated best in FIG. 4. A small ledge 36 is formed adjacent each projection 34 in alignment with the distal tip of each projection 34. The distance between a distal tip of a projection 34 and its corresponding land 36 is slightly smaller than the distance between the distal tip and proximal portion 38 of the projection. Projections 34 are preferably integral with body 26 and may flex a small amount. A recess 40 is formed in each side 42 of body 26.

To use the perpendicular rod system 10, a surgeon first installs a pair of pedicle screws 12 into the pedicle portions of the vertebra such that the heads 16 of the screws are in alignment. A rod 18 is connected between screws 12 preferably by use of a compression sleeve 20 and collar 22. Rod 12 may be bent slightly to accommodate the contour of the vertebra. Screws 12 and rod 18 constitute a primary fixation point for the system 10. A plurality of such primary fixation points will typically be required along the length of the spine. The surgeon next connects a perpendicular rod connector 24 to rod 16 in the following manner. Griping the connector with an instrument engaged within recesses 40, the surgeon positions the connector transverse to rod 26 such that the rod is adjacent back wall 32 between projection 34 as shown in FIG. 5. The connector 24 is rotated in the direction of arrows 44 to force the distal tips of projections 34 over rod 26. The distance between the distal tips of projections 34 and their corresponding ledges 36 is slightly smaller than the diameter of rod 26. Therefore, as the connector is rotated in the direction of arrows 44, projections 34 yield to allow the rod to fully seat within the projections. Each projection 34 is dimensioned so as to accommodate the rod in a relaxed state. Once connector 24 is connected to rod 18, it may be slid along the rod for proper lateral positioning with the spinal rod 30. Rod 30 is then connected to connector 24 preferably by a wedge fit between a sleeve 20 and the C-shaped body 26 of connector 24. In the preferred embodiment, the sleeve is maintained in position by a collar 22 as mentioned previously. Typically, a second connector 24 will be attached to rod 18 for connection of a second spinal rod 30. Perpendicular connector 24 therefor forms a secondary fixation point in the system 10 of the invention. The secondary fixation point may be slid along rod 16 to accommodate lateral positioning of the spinal rods.

An alternative embodiment of the system is illustrated in FIG. 8. A common numbering scheme is used between FIGS. 1-7 and FIG. 8 wherein a common number indicates similar function and structure. System 10, illustrated in FIG. 8, includes a pair of pedicle screws 48 having a threaded shaft and a generally C-shaped head as with screw 12 of FIGS. 1-7. However, screw 48 is bent at its neck 52 such that the head and shaft are out of longitudinal alignment by approximately 20 degrees. When screws 48 are turned into the pedicle portion of a vertebra, the heads are positioned at an angle such that bar 50 does not need to be bent to connect the two screws. Connectors 24 may be connected to the rod in a manner described above.

It should be understood that while the above invention has been described as using sleeves and collars to attach the rods to the screws and connectors, such should not be considered a limitation on the invention of providing primary and secondary fixation points. Indeed, many other viable alternatives well known in the industry may find use in connecting the rods to the screws and connectors.

Further, it should be understood that the invention is not to be limited to the precise forms disclosed but may be modified in keeping with the appended claims.

We claim:

1. A system for functionally connecting a spinal rod to a vertebra, said system comprising a first fixation means connected to said vertebra, said first fixation means includes a bar carried transverse to a longitudinal dimension of a patients's spinal column, said system further including a secondary fixation means carried by said bar, said secondary fixation means being shiftable on said bar relative to said first fixation means, and means for connecting said spinal rod to said secondary fixation means such that said spinal rod is transverse to said bar, wherein said secondary fixation means comprises a connector having a body with an opening for accommodating said spinal fixation rod, a pair of hooks extend outwardly from a wall of said body, said hooks clampingly engage said bar such that said spinal fixation rod is transverse to said bar.

2. The system of claim 1 wherein said first fixation means includes at least two screws for seating within each pedicle portion of said vertebra, said bar extending between said screws.

3. The system of claim 1 wherein said connector includes a ledge adjacent each hook, said hooks extending from said wall such that said hooks face in opposite directions and are spaced from one another along said wall, said hooks yield to accept said oar.

* * * * *